United States Patent
Yoshino et al.

(10) Patent No.: US 9,738,654 B2
(45) Date of Patent: Aug. 22, 2017

(54) METHOD FOR PRODUCING NITROGEN-CONTAINING HETEROCYCLIC N-OXIDE COMPOUND

(71) Applicant: NISSAN CHEMICAL INDUSTRIES, LTD., Tokyo (JP)

(72) Inventors: Hironobu Yoshino, Funabashi (JP);
Kenichi Seki, Sanyo-Onoda (JP);
Hirohide Kitsuyama, Funabashi (JP);
Ikumasa Hidaka, Sanyo-Onoda (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/431,258

(22) PCT Filed: Sep. 13, 2013

(86) PCT No.: PCT/JP2013/074867
§ 371 (c)(1),
(2) Date: Mar. 25, 2015

(87) PCT Pub. No.: WO2014/050613
PCT Pub. Date: Apr. 3, 2014

(65) Prior Publication Data
US 2015/0266887 A1    Sep. 24, 2015

(30) Foreign Application Priority Data

Sep. 27, 2012  (JP) .................................. 2012-215045

(51) Int. Cl.
C07D 491/052    (2006.01)

(52) U.S. Cl.
CPC .................. *C07D 491/052* (2013.01)

(58) Field of Classification Search
CPC ................................ C07D 491/052
USPC ...................................... 546/89
See application file for complete search history.

(56) References Cited

U.S. PATENT DOCUMENTS

| | | | |
|---|---|---|---|
| 2006/0100200 A1 | 5/2006 | Meyer et al. | |
| 2008/0004262 A1 | 1/2008 | Ohrai et al. | |
| 2010/0069374 A1 | 3/2010 | Ohrai et al. | |

FOREIGN PATENT DOCUMENTS

| | | | |
|---|---|---|---|
| JP | 2005255560 A | 9/2005 | |
| JP | 2007530436 A | 11/2007 | |
| JP | 2008519004 A | 6/2008 | |
| WO | 2005090357 A1 | 9/2005 | |

OTHER PUBLICATIONS

Franklin Davis, 1988, Chemistry of Oxaziridines.*
Dec. 17, 2013 International Search Report issue in International Application No. PCT/JP2013/074867.
Dec. 17, 2013 Written Opinion issued in International Application No. PCT/JP2013/074867.
Mosher et al., "Working With Hazardous Chemicals," Organic Syntheses, Coll. vol. 4, p. 828, 1963; vol. 33, p. 79, 1953.
Payack et al., "A Concise Synthesis of a Novel Antiangiogenic Tyrosine Kinase Inhibitor," J. Org. Chem,vol. 70, 2005, pp. 175-178.
Kennedy et al., "The Oxidation of Organic Substances by Potassium Peroxymonosulfate," Nov. 1960, vol. 25, pp. 1901-1906.
Azami et al., "Synthesis and Antibacterial Activity of Novel 4-Pyrrolidinylthio Carbapenems Part IV. 2-Alkyl Substituents Containing Cationic Heteroaromatics Linked via a C-C Bond," Bioorganic & Medicinal Chemistry, vol. 9, 2001, pp. 961-982.
Pailloux et al., "Oxidation Reactivity Channels for 2-(Pyridin-2-yl)-N,N-diphenylacetamides," Journal of Organic Chemistry, 2007, vol. 72, pp. 9195-9202.
Murray et al., "Dioxiranes: Synthesis and Reactions of Methyldioxiranes," Journal of Organic Chemistry, 1985, vol. 50, pp. 2847-2853.
Mar. 31, 2016 Office Action issued in Chinese Application No. 201380040269.6.

\* cited by examiner

*Primary Examiner* — Rita Desai
(74) *Attorney, Agent, or Firm* — Oliff PLC

(57) ABSTRACT

The problem of the present invention is to provide a production method for safely synthesizing a nitrogen-containing heterocyclic N-oxide compound in high yield. Another problem of the present invention is to provide a novel N-oxide compound. There is provided a method for producing a nitrogen-containing heterocyclic N-oxide compound of Formula (2), such as 2,2,7,9-tetramethyl-2H-pyrano[2,3-g]quinoline N-oxide, by oxidizing a nitrogen-containing heterocyclic compound of Formula (1), such as 2,2,7,9-tetramethyl-2H-pyrano[2,3-g]quinoline with a persulfate.

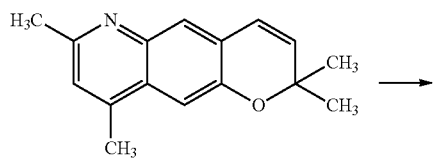

(1)

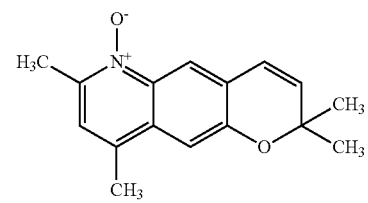

(2)

14 Claims, No Drawings

METHOD FOR PRODUCING NITROGEN-CONTAINING HETEROCYCLIC N-OXIDE COMPOUND

TECHNICAL FIELD

The present invention relates to a novel method for producing a nitrogen-containing heterocyclic N-oxide compound by N-oxidation reaction of a nitrogen-containing heterocyclic compound, and a novel N-oxide compound.

BACKGROUND ART (3R*,4S*)-7-hydroxymethyl-2,2,9-trimethyl-4-(phenethylamino)-3,4-dihydro-2H-pyrano[2,3-g]quinolin-3-ol (compound (3)) has an anti-arrhythmic action, and its possible use as a pharmaceutical product has been known (e.g., see Patent Document 1).

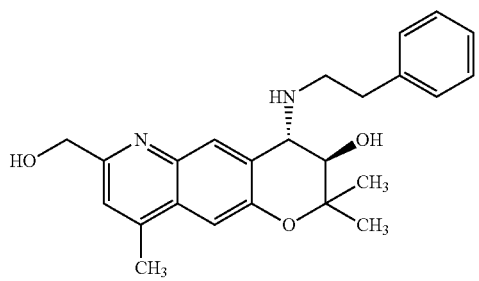

(3)

As a method for synthesizing the compound (3), a method is known in which 2,2,7,9-tetramethyl-2H-pyrano[2,3-g]quinoline (compound (1)) is reacted with m-chloroperbenzoic acid, followed by a reaction with acetic anhydride to obtain (2,2,9-trimethyl-2H-pyrano[2,3-g]quinolin-7-yl)-methyl acetate (compound (6)), as shown in the following reaction formula (I), and the compound (6) is transferred to the compound (3). In a reaction of the reaction formula (I), it is presumed that the compound (1) is oxidized by m-chloroperbenzoic acid to produce 2,2,7,9-tetramethyl-2H-pyrano[2,3-g]quinoline 6-oxide (compound (2)) in which the nitrogen atom in the quinoline ring is N-oxidized. However, the details of the reaction were not clear.

In the production method through the reaction formula (I), m-chloroperbenzoic acid is used as an oxidizing agent. m-Chloroperbenzoic acid is a hazardous reagent, which is classified as Class 5.2 (organic peroxides) of the UN Recommendations on the Transport of Dangerous Goods, and care is necessary in use on an industrial scale.

Therefore, in order to establish a method for industrially producing the compound (3), the establishment of a method for producing the compound (2), in particular, a method that enables safe, large-volume production without a hazardous reagent such as m-chloroperbenzoic acid has been required.

Reaction Formula (I)

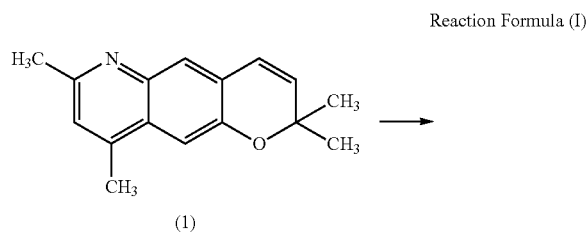

(1)

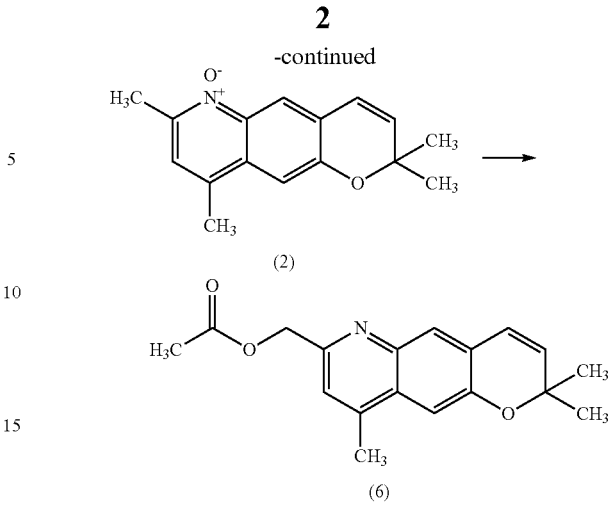

For synthesis of a N-oxide compound such as a pyridine ring and a quinoline ring that are generally a nitrogen-containing heterocycle, an oxidation process using peracetic acid (e.g., see Non-Patent Document 1), and an oxidation process using rare metal or heavy metal as a catalyst and hydrogen peroxide (e.g., see Non-Patent Documents 2 and 3) are known. However, the processes have a problem in safety of an oxidizing agent.

As a safe oxidizing agent capable of causing an N-oxidation reaction, OXONE (registered trademark by DuPont Co.) is known. OXONE is a white crystal that is a double salt of potassium hydrogen persulfate-potassium hydrogen sulfate-potassium sulfate, and is an excellent oxidizing agent that is industrially handled with ease. As an N-oxidation reaction using OXONE, a reaction method using only OXONE is known. However, the yield in this reaction is very low (see, Non-Patent Document 4). As another example of the N-oxidation reaction using OXONE, a method of improving the reactivity by addition of a base is known. However, the details of this reaction are not clear, and in particular, a method of using the base and an effect thereof are not established, for example, the equivalent weight of base to be used is excessive or insufficient for OXONE (e.g., see Non-Patent Documents 5 and 6). As further another example of the N-oxidation reaction using OXONE, a method of improving the reactivity by further addition of acetone is also known (e.g., see Non-Patent Document 7). However, dimethyl dioxirane that is a hazardous peroxide is considered to be produced during this reaction, and therefore this method has a problem of unsuitability as an industrial production method.

PRIOR ART DOCUMENTS

Patent Document

Patent Document 1: WO 2005/090357

Non-Patent Documents

Non-Patent Document 1: Org. Synth., Coll. Vol. 4, 828 (1963), Vol. 33, 79(1953)
Non-Patent Document 2: Josepf F. P. et al., J. Org. Chem., 2005, 70, 175-178
Non-Patent Document 3: JP 2005-255560 A
Non-Patent Document 4: Richard J. K. and Albert M. S., J., Org. Chem. 1960, 25, 1901-1906

Non-Patent Document 5: Azami H. et al., Bioorg. Med. Chem., 2001, 9, 961-982
Non-Patent Document 6: Sylvie P. et al., J. Org. Chem., 2007, 72, 9195-9202
Non-Patent Document 7: Murray R. W. et al., J. Org. Chem., 1985, 50, 2847-2853

SUMMARY OF THE INVENTION

Problem to be Solved by the Invention

It is an object of the present invention to provide a production method for safely synthesizing a nitrogen-containing heterocyclic N-oxide compound in high yield. Another object of the present invention is to provide a novel N-oxide compound.

Means for Solving Problem

The inventors of the present invention have intensively studied, and as a result, found that a compound (2) is obtained by oxidation of a compound (1) using a persulfate and this oxidation reaction is promoted by adding a basic compound to a reaction system. Since the compound (1) has an olefin structure, an epoxidation reaction of olefin is caused as a side reaction in addition to the N-oxidation reaction, and compounds such as the following compounds (4) and (5) are produced as byproducts.

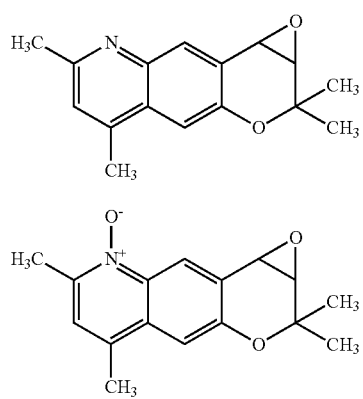

This epoxidation as the side reaction is an oxidation reaction that is the same as N-oxidation as a major reaction. Therefore, selectivity may not be improved by merely adjusting the strength of an oxidizing agent. The inventors have found that by adjusting the pH of a reaction mixed solution, a reaction with little side reaction and high selectivity of N-oxidation can be caused. Thus, the present invention has been accomplished. Specifically, the present invention is characterized as follows:

(I)
A method for producing a quinoline N-oxide compound of Formula (B) by reacting a quinoline compound of Formula (A) with a persulfate:

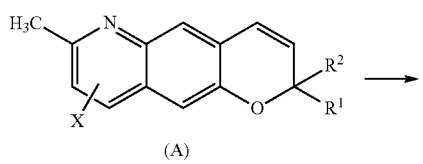

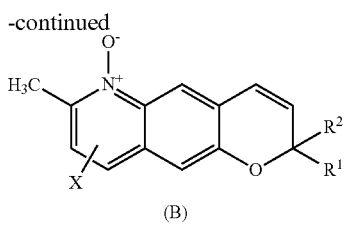

(In the formula, $R^1$ and $R^2$ are each independently a hydrogen atom, a $C_{1-6}$ alkyl group, or a $C_{7-12}$ aralkyl group; and X is a hydrogen atom, a halogen atom, a $C_{1-6}$ alkyl group, a $C_{3-6}$ cycloalkyl group, a $C_{6-10}$ aryl group, a $C_{7-12}$ aralkyl group, a $C_{1-6}$ alkoxy group, a $C_{1-6}$ acyloxy group, or a cyano group).

(II)
The method according to the item (I), wherein the quinoline compound of Formula (A) is 2,2,7,9-tetramethyl-2H-pyrano[2,3-g]quinoline of Formula (1) and the quinoline N-oxide compound of Formula (B) is 2,2,7,9-tetramethyl-2H-pyrano[2,3-g]quinoline N-oxide of Formula (2)

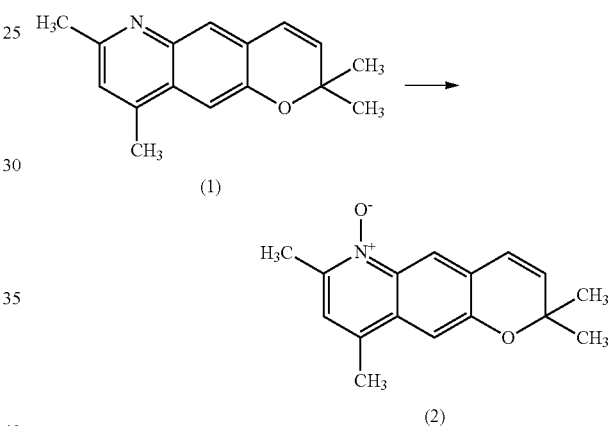

(III)
The method according to the item (I) or (II), comprising adding a base.
(IV)
The method according to the item (III), wherein the base added is a hydroxide of alkali metal.
(V)
The method according to the item (IV), wherein the base added is potassium hydroxide.
(VI)
The method according to any one of the items (III) to (V), wherein the base added is an aqueous solution form of the base.
(VII)
The method according to any one of the items (I) to (VI), comprising adjusting the pH of a reaction solution to 6 to 7.
(VIII)
The method according to any one of the items (I) to (VII), wherein the persulfate is potassium hydrogen persulfate.
(IX)
The method according to any one of the items (I) to (VII), wherein the persulfate is a double salt containing potassium hydrogen persulfate.
(X)
The method according to the item (IX), wherein the double salt containing potassium hydrogen persulfate is a double salt of potassium hydrogen persulfate, potassium hydrogen sulfate, and potassium sulfate.
(XI)
The method according to any one of the items (I) to (X), wherein the persulfate added has an aqueous solution form.
(XII)
2,2,7,9-tetramethyl-2H-pyrano[2,3-g]quinoline 6-oxide of Formula (2)

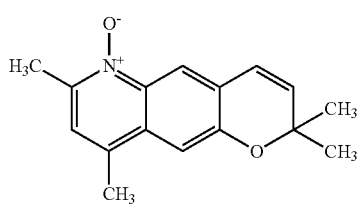

(2)

MODES FOR CARRYING OUT THE INVENTION

As a compound usable in a production method of the present invention, a compound of Formula (A) can be used in addition to the compound (1).

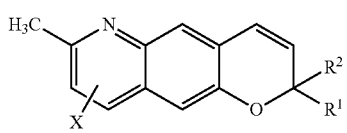

(A)

(In the formula, $R^1$ and $R^2$ are each independently a hydrogen atom, a $C_{1-6}$ alkyl group, or a $C_{7-12}$ aralkyl group; and X is a hydrogen atom, a halogen atom, a $C_{1-6}$ alkyl group, a $C_{6-10}$ aryl group, a $C_{7-12}$ aralkyl group, a $C_{1-6}$ alkoxy group, a $C_{1-6}$ acyloxy group, or a cyano group.)

A substituent in the present invention will be described.

A halogen atom refers to fluorine, chlorine, bromine, or iodine.

The concept of an alkyl group in the present invention includes a linear alkyl group and a branched alkyl group.

A $C_{1-6}$ alkyl group refers to an alkyl group having a carbon atom number of 1 to 6. Examples thereof include a methyl group, an ethyl group, a n-propyl group, an isopropyl group, a n-butyl group, an isobutyl group, a sec-butyl group, a tert-butyl group, a n-pentyl group, and a n-hexyl group.

The $C_{1-6}$ alkyl group in the present invention is preferably a $C_{1-3}$ alkyl group, that is, an alkyl group having a carbon atom number of 1 to 3, and more preferably a methyl group.

A $C_{3-6}$ cycloalkyl group refers to a cycloalkyl group having a carbon atom number of 3 to 6. Examples thereof include a cyclopropyl group, a cyclobutyl group, and a cyclohexyl group.

The $C_{3-6}$ cycloalkyl group in the present invention is preferably a cyclopropyl group.

A $C_{6-10}$ aryl group refers to an aryl group having a carbon atom number of 6 to 10.

Examples thereof include a phenyl group and a naphthyl group.

The $C_{6-10}$ aryl group in the present invention is preferably a phenyl group.

A $C_{7-12}$ aralkyl group refers to a group in which the $C_{1-6}$ alkyl group is substituted with one phenyl group. The phenyl group may substitute on any position of the $C_{1-6}$ alkyl group. Examples of the aralkyl group include a benzyl group, a phenylethyl group, a phenylpropyl group, and a phenylbutyl group.

The $C_{7-12}$ aralkyl group in the present invention is preferably a benzyl group.

A $C_{1-6}$ alkoxy group refers to an oxy group substituted by the $C_{1-6}$ alkyl group. Examples thereof include a methoxy group, an ethoxy group, an isopropoxy group, and a tert-butoxy group.

The $C_{1-6}$ alkoxy group in the present invention is preferably a $C_{1-3}$ alkoxy group, that is, an oxy group substituted by a $C_{1-3}$ alkyl group, and more preferably a methoxy group.

A $C_{1-6}$ acyloxy group refers to a carbonyloxy group substituted by the $C_{1-6}$ alkyl group. Examples thereof include an acetoxy group ($CH_3C(=O)O-$ group).

The $C_{1-6}$ acyloxy group in the present invention is preferably an acetoxy group.

As the compound of Formula (A) and the compound of Formula (1) (hereinafter referred to as a reactant) that are used as a raw material in the method of the present invention, a free form thereof may be used, or an acid salt or solvate thereof may be used as long as it does not prevent reaction. Examples of the acid salt of the reactant include a hydrohalogenic acid salt (e.g., hydrochloride, and hydrobromide), a sulfonate (e.g., sulfate, methanesulfonate, and tosylate), a phosphate (e.g., phosphate), and a carboxylate (e.g., acetate, benzoate, and maleate). Preferred examples of the acid salt may include a carboxylate, and particularly preferably maleate.

In the method of present invention, the reactant may be dissolved or suspended in a solvent.

A solvent usable in the method of present invention is not particularly limited as long as it does not prevent this reaction. It is preferable that water, an alcohol solvent (e.g., methanol, ethanol, and isopropanol), a halogen-containing hydrocarbon solvent (e.g., methylene chloride), a carboxylic acid solvent (e.g., acetic acid, and trifluoroacetic acid), a sulfonic acid solvent (e.g., methanesulfonic acid), a phosphoric acid solvent (e.g., phosphoric acid), an aromatic hydrocarbon solvent (e.g., benzene, toluene, and xylene), an aliphatic hydrocarbon solvent (e.g., hexane, and heptane), an amide solvent (e.g., N,N-dimethylformamide, and N,N-dimethylacetamide), a nitrile solvent (e.g., acetonitrile), a sulfone solvent (e.g., dimethyl sulfone), a sulfoxide solvent (e.g., dimethyl sulfoxide), 1,4-dioxane, or cyclopentyl methyl ether be used since a peroxide is unlikely to be produced in the presence of a persulfate.

The solvent may be used alone or in a mixture of two or more thereof.

In order to dissolve both the persulfate and the reactant, it is preferable that water and a water-soluble organic solvent be used in combination. Herein, water-soluble means that a substance can be completely dissolved in water at any ratio. The water-soluble organic solvent is preferably a water-soluble alcohol solvent, a water-soluble amide solvent, or a water-soluble carboxylic acid solvent, more preferably a water-soluble alcohol solvent, and particularly preferably methanol.

The reaction can be caused using water in combination with a water-insoluble solvent in the presence of a phase transfer catalyst in a two-layer system. Examples of a phase transfer catalyst used in the present invention include an ammonium salt (e.g., tetrabutylammonium bromide), and a phosphonium salt (e.g., tetrabutylphosphonium bromide).

The amount of the solvent to be used is not particularly limited, and is 0.1 parts by mass to 1,000 parts by mass, preferably 1 part by mass to 100 parts by mass, and more preferably 3 parts by mass to 20 parts by mass, relative to the mass of the reactant.

Examples of the persulfate used in the method of the present invention include an alkali metal persulfate (e.g., sodium persulfate, and potassium persulfate), an ammonium persulfate, and a hydrogen persulfate (e.g., sodium hydrogen persulfate, potassium hydrogen persulfate, and ammonium hydrogen persulfate).

The persulfate is preferably a hydrogen persulfate, more preferably an alkali metal hydrogen persulfate, and further preferably potassium hydrogen persulfate.

As the persulfate used in the method of the present invention, a double salt of the persulfate can be used. The double salt refers to a salt containing two or more kinds of cations, two or more kinds of anions, or two or more kinds of cations and two or more kinds of anions.

A double salt of the persulfate used in the method of the present invention is preferably a double salt of hydrogen persulfate, more preferably a double salt of potassium hydrogen persulfate, potassium hydrogen sulfate, and potassium sulfate, and further preferably commercially available OXONE (registered trademark by DuPont Co.) of $2KHSO_5 \cdot KHSO_4 \cdot K_2SO_4$. Further, the persulfates may be prepared in a reaction system using ammonium persulfate or persulfuric acid as a raw material and used.

The persulfate is used in an amount of 1 mol to 10 mol, preferably 1 mol to 5 mol, and further preferably 1 mol to 3 mol, relative to 1 mol of the reaction substrate.

One mol of OXONE includes 2 mol of potassium hydrogen persulfate. The amount by mol of OXONE in the following Examples is represented as a double salt with a molecular weight of 614.76.

Since an aqueous solution of the persulfate is acidic, the pH can be adjusted by adding a base as a solid or a solution thereof. A base usable in the reaction is not particularly limited as long as it does not prevent this reaction. A hydroxide (e.g., sodium hydroxide, and potassium hydroxide), a bicarbonate (e.g., sodium bicarbonate, and potassium bicarbonate), a carbonate (e.g., sodium carbonate, and potassium carbonate), a phosphate (e.g., sodium phosphate, disodium hydrogen phosphate, sodium dihydrogen phosphate, potassium phosphate, dipotassium hydrogen phosphate, and potassium dihydrogen phosphate), an acetate (e.g., sodium acetate, and potassium acetate), an amine (e.g., a tertiary amine such as triethylamine), or aqueous ammonia can be used. Due to the basic strength thereof and no generation of gas during neutralization, a hydroxide is preferably used, a hydroxide of alkali metal is further preferably used, and potassium hydroxide is particularly preferably used.

In the present invention, a hydrogen ion concentration index is represented as pH. The pH in the present invention is not restricted to the hydrogen ion concentration index of an aqueous solution, and the concept includes the hydrogen ion concentration index of a solvent other than water, a mixed solvent of water and the water-soluble organic solvent, and a solution or suspension containing the solvents.

The base is used in an amount of 1 mol to 10 mol, preferably 1 mol to 5 mol, and further preferably 1 mol to 3 mol, relative to 1 mol of the reactant.

The persulfate used in the method of the present invention is water-soluble, and the reactant is lipophilic. For this reason, a mixed solvent of water and the water-soluble organic solvent may be used to dissolve both the reactant and the persulfate and efficiently promote the reaction. At this time, the reactant and the persulfate partly remain without dissolving in a state of suspension at the outset of the reaction, and then are dissolved with progression of the reaction.

In the method of the present invention, a suspended persulfate may be dissolved with progression of the reaction, to decrease the pH of the reaction solution in the reaction. In this case, the pH of the reaction solution is adjusted by adding a base to the reaction solution. Thus, the pH can be maintained at a constant range.

The pH of the reaction solution is preferably maintained at 4 to 8, more preferably at 5 to 7, and further preferably at 6 to 7.

Examples of a method of adjusting the pH include a method A: of adding the persulfate and the base to a reactor containing the reactant, a method B: of adding the reactant and the base to a reactor containing the persulfate, and a method C: of adding the reactant and the persulfate to a reactor containing the base. Since the persulfate can be supplied while consumption thereof is always confirmed, the methods A and C are preferred in terms of safety, and the method A is further preferred.

An order of adding the persulfate and the base to the reactant may be an order of adding the whole amounts of the persulfate and the base in turn or an order of adding the persulfate and the base together. The order of adding the persulfate and the base together is preferred.

Alternatively, a portion of the persulfate or the base may be first added until the pH reaches a target pH, and the rest may be then added together. It is desirable that the persulfate and the base be gradually added while the progression of the reaction, the generation of oxygen gas, and heat generation are controlled. When the persulfate and the base are added together, it is preferable that the persulfate and the base be not mixed using separate dropping devices or input ports before they reach the solution or suspension of the reactant.

When the acid salt of the reactant is used, the base is added to the solution of the reactant, and the persulfate and the base can be added together. When the pH of the reaction solution decreases after completion of addition of the persulfate, the base is gradually added to maintain the pH.

The time required for addition of the persulfate is not particularly limited, and is a time sufficient to control the progression of the reaction, the generation of oxygen gas, and heat generation, 0.5 hours to 8 hours, and preferably 2 hours to 4 hours.

The reaction temperature in the present invention is not particularly limited, and preferably falls within a range of $-10°$ C. to $120°$ C., more preferably $0°$ C. to $100°$ C., and further preferably $10°$ C. to $40°$ C.

The reaction time in the present invention is not limited as long as it is sufficient to consume the reaction substrate, and is preferably 10 minutes to 24 hours, and more preferably 30 minutes to 6 hours.

The N-oxide compound obtained by the method of the present invention may be isolated or used in a solution form as it is at the next production process. The conditions of the solution, such as the content of the N-oxide compound in the solution, can be quantitatively analyzed by an analysis method such as HPLC, and the yield in the reaction can be measured by quantitative analysis.

EXAMPLES

Hereinafter, the present invention will be described specifically with reference to Examples, but the scope of the present invention is not limited to these Examples.

In Examples, NMR means nuclear magnetic resonance, and HPLC means high performance liquid chromatography.

The purity of each compound by HPLC analysis is represented by an area percentage method of expressing the ratio of a target peak area in the whole peak area in percentage.

The pH of a reaction solution can be measured by a method familiar to those skilled in the art. For example, a solution or mixed solution in a reaction is directly measured with a pH meter or a small amount of the solution or mixed solution is sampled and measured with a pH meter or a pH test paper.

In Examples, ECP300 manufactured by JEOL Ltd. was used for NMR analysis, and B-545 manufactured by SIBATA SCIENTIFIC TECHNOLOGY LTD. was used for measurement of melting point.

HPLC analysis was performed using LC-10Avp manufactured by Shimadzu Corporation under the following conditions.
Column: L-column ODS (available from Chemicals Evaluation and Research Institute, Japan, 4.6 mm in diameter× 250 mm in length, particle diameter: 5 μm)
Eluent: 450 mL of acetonitrile and 550 mL of 0.01 M acetic acid buffer (pH: 3.8) were mixed and 1.4 g of sodium dodecylsulfate was dissolved in the mixture. As the 0.01 M acetic acid buffer, a mixture of 800 mL of 0.01 M acetic acid aqueous solution and 100 mL of 0.01 M sodium acetate solution was used.
Flow rate: 1.0 mL/min
Column Temperature: 40° C.
Wavelength of ultraviolet-visible spectroscopy: 254 nm Reference Synthesis Example 1

Production of 2,2,7,9-tetramethyl-2H-pyrano[2,3-g]quinoline maleate

N-(2,2,-dimethyl-2H-chromen-6-yl)acetamide (199.38 g, 0.918 mol), 1-propanol (800 g), and hydrochloric acid (288 g) were mixed and heated to reflux at 90° C. to 95° C. for 5 hours. The mixture was cooled to room temperature, iron chloride (anhydrous) (400 g, 2.49 mol) was added, and the mixture was heated to 90° C. To the mixture, 3-penten-2-one (140 g, 1.66 mol) was added dropwise and the mixture was heated for 2 hours. The mixture was cooled to room temperature, toluene (1,100 g) and water (1,399 g) were added, and the mixture was separated. To the obtained organic phase, a 16% sodium carbonate aqueous solution (2,200 g) and water (901 g) were added, and the mixture was separated. To the obtained organic phase, activated carbon (10 g) was added, and the mixture was stirred and filtrated. From the filtrate, the solvent was evaporated, and the residue was dried and solidified. The residue was dissolved in ethyl acetate (801 g) and toluene (108 g), and the mixture was heated to 50° C. To the mixture, a solution of maleic acid (85.5 g, 0.737 mol) dissolved in methanol (200 g) was added dropwise. The mixture was cooled to 20° C., and the precipitated crystal was collected by filtration, washed with ethyl acetate (201 g), and dried under reduced pressure at 50° C. to obtain 204.77 g (yield: 62.8%) of 2,2,7,9-tetramethyl-2H-pyrano[2,3-g]quinoline maleate as a yellow solid.
Appearance: yellow solid
$^1$H-NMR (CDCl$_3$, TMS)
δ(ppm): 1.53 (6H, s), 2.76 (3H, s), 2.91 (3H, s), 6.09 (1H, d, J=9.9 Hz), 6.40 (2H, s), 6.63 (1H, d, J=9.9 Hz), 7.30 (2H, s), 8.09 (1H, s)
Melting Point: 175° C.

Example 1

Production of 2,2,7,9-tetramethyl-2H-pyrano[2,3-g]quinoline 6-oxide

Methanol (25.0 g) and a 50% potassium hydroxide aqueous solution (1.52 g, 13.5 mmol) were added to 2,2,7,9-tetramethyl-2H-pyrano[2,3-g]quinoline maleate (5.01 g, purity: 96%, 13.5 mmol), and the mixture was stirred at 21° C. for 20 minutes. A solution of OXONE (9.55 g, 15.5 mmol) in water (30 g) was added dropwise over 30 minutes, and at the same time, a 50% potassium hydroxide aqueous solution was added dropwise while being adjusted so that the temperature and the pH of the reaction solution were maintained at 21° C. to 27° C. and 6 to 7, respectively. After completion of dropwise addition of the OXONE aqueous solution, the mixture was stirred for 3 hours while the pH was maintained at 6 to 7 by dropwise addition of 50% potassium hydroxide aqueous solution.

After the reaction, an insoluble substance was filtered and washed with chloroform (15.0 g) twice. To the resulting filtrate, a 50% potassium hydroxide aqueous solution (0.76 g, 6.8 mmol) was added, and the mixture was separated to obtain a solution of 2,2,7,9-tetramethyl-2H-pyrano[2,3-g] quinoline 6-oxide in chloroform. This solution was quantitatively analyzed by HPLC to calculate the yield. The yield was 89.6%. The peak areas (%) of the compounds (1), (2), (4), and (5) in the solution are shown in Table 1.

TABLE 1

| | 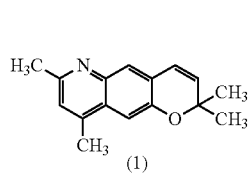 (1) | 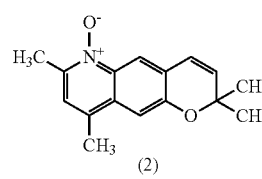 (2) | 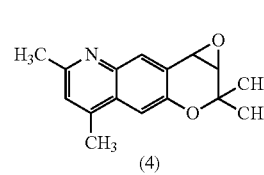 (4) | 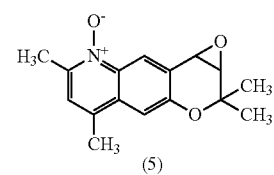 (5) |
|---|---|---|---|---|
| 1 hour of reaction | 4.761 | 85.983 | 0.161 | 3.685 |
| 2 hours of reaction | 2.117 | 86.908 | 0.099 | 5.448 |

TABLE 1-continued

| 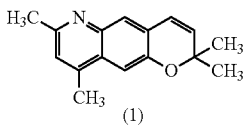 (1) | 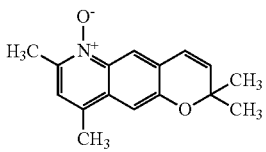 (2) | 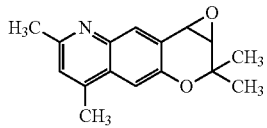 (4) | 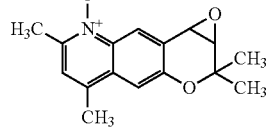 (5) |
|---|---|---|---|
| 1.329 | 86.400 | 0.077 | 6.708 |

3 hours of reaction

This solution was purified by silica gel chromatography to obtain target 2,2,7,9-tetramethyl-2H-pyrano[2,3-g]quinoline 6-oxide.

Appearance: yellow solid $^1$H-NMR (CDCl$_3$, TMS)

δ(ppm): 1.50 (6H, s), 2.51 (3H, s), 2.63 (3H, s), 5.93 (1H, d, J=9.9 Hz), 6.61 (1H, d, J=9.9 Hz), 7.02 (1H, s), 7.16 (1H, s), 8.42 (1H, s)

Melting Point: 187° C.

Example 2

Methanol (25.1 g) and a 50% potassium hydroxide aqueous solution (1.52 g, 13.5 mmol) were added to 2,2,7,9-tetramethyl-2H-pyrano[2,3-g]quinoline maleate (5.00 g, purity: 96%, 13.5 mmol), and the mixture was stirred at 21° C. to 22° C. for 30 minutes. A solution of OXONE (9.56 g, 15.5 mmol) in water (30.6 g) was added dropwise over 30 minutes, and at the same time, a 50% potassium hydroxide aqueous solution was added dropwise while being adjusted so that the temperature and the pH were maintained at 22° C. to 23° C. and 5 to 6, respectively. After completion of dropwise addition of the OXONE aqueous solution, the mixture was stirred for 6 hours while the pH was maintained at 5 to 6 by dropwise addition of 50% potassium hydroxide aqueous solution.

After the reaction, an insoluble substance was filtered and washed with chloroform (15.0 g) twice. To the resulting filtrate, a 50% potassium hydroxide aqueous solution (0.76 g, 6.8 mmol) was added, and the mixture was separated to obtain a solution of 2,2,7,9-tetramethyl-2H-pyrano[2,3-g]quinoline 6-oxide in chloroform. This solution was quantitatively analyzed by HPLC to calculate the yield. The yield was 75.2%. The peak areas (%) of the compounds (1), (2), (4), and (5) in the solution are shown in Table 2. The raw materials are almost consumed and the target favorably increases. However, the production amount of the compound (5) as an impurity is larger as compared with Example 1.

TABLE 2

| 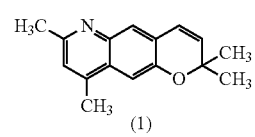 (1) | 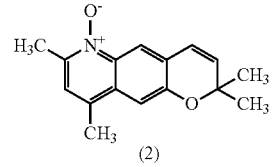 (2) | 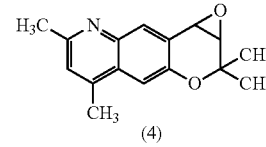 (4) | 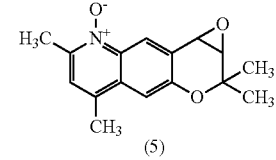 (5) |
|---|---|---|---|
| 11.377 | 78.017 | 0.268 | 5.123 |
| 5.596 | 80.705 | 0.175 | 8.114 |
| 4.057 | 79.952 | 0.147 | 10.195 |
| 3.101 | 78.743 | 0.148 | 11.972 |

1 hour of reaction 2 hours of reaction 3 hours of reaction 4 hours of reaction

TABLE 2-continued

| | | | |
|---|---|---|---|
| 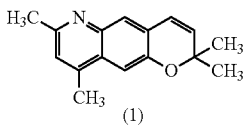 (1) | 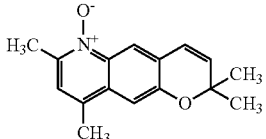 (2) | 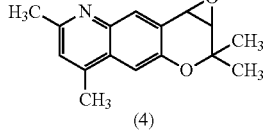 (4) | 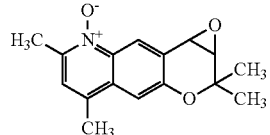 (5) |
| 5 hours of reaction | 2.362 | 77.823 | 0.125 | 13.470 |
| 6 hours of reaction | 2.079 | 76.418 | 0.139 | 14.625 |

Example 3

Methanol (25.0 g) and a 50% potassium hydroxide aqueous solution (1.52 g, 13.5 mmol) were added to 2,2,7,9-tetramethyl-2H-pyrano[2,3-g]quinoline maleate (5.00 g, purity: 96%, 13.5 mmol), and the mixture was stirred at 21° C. for 30 minutes. A solution of OXONE (9.55 g, 15.5 mmol) in water (30.6 g) was added dropwise over 20 minutes, and at the same time, a 50% potassium hydroxide aqueous solution was added dropwise while being adjusted so that the temperature and the pH were maintained at 22° C. to 28° C. and 7 to 8, respectively. After completion of dropwise addition of the OXONE aqueous solution, the mixture was stirred at 24° C. to 26° C. for 7 hours.

The peak areas (%) of the compounds (1), (2), (4), and (5) in the reaction solution are shown in Table 3. The side reaction is suppressed and the target favorably increases. However, the amount of remained compound (1) as the raw material is larger as compared with Example 1.

TABLE 3

| | | | |
|---|---|---|---|
| 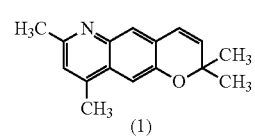 (1) | 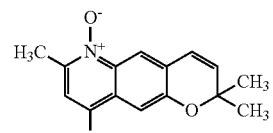 (2) | 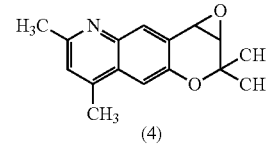 (4) | 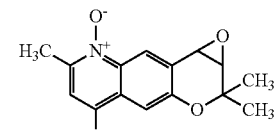 (5) |
| 1 hour of reaction | 22.389 | 70.792 | 0.432 | 1.352 |
| 2 hours of reaction | 18.233 | 74.482 | 0.376 | 1.757 |
| 3 hours of reaction | 17.022 | 75.475 | 0.347 | 1.984 |
| 4 hours of reaction | 16.423 | 75.848 | 0.324 | 2.137 |
| 5 hours of reaction | 16.061 | 76.050 | 0.304 | 2.242 |
| 7 hours of reaction | 15.688 | 76.222 | 0.273 | 2.351 |

Example 4

Methanol (25.0 g) and a 50% potassium hydroxide aqueous solution (3.05 g, 27.2 mmol) were added to 2,2,7,9-tetramethyl-2H-pyrano[2,3-g]quinoline maleate (5.00 g, purity: 96%, 13.5 mmol), and the mixture was stirred at 25° C. to 29° C. for 30 minutes. A solution of OXONE (7.89 g, 12.8 mmol) in water (27.5 g) was added dropwise at 27 to 30° C. over 2 hours. The mixture was stirred at 28 to 30° C. for 27 hours. During the reaction, the pH changed between 2 to 3.

After the reaction, an insoluble substance was filtered and washed with 15.0 g of chloroform twice. The mixture was separated to obtain a solution of 2,2,7,9-tetramethyl-2H-pyrano[2,3-g]quinoline 6-oxide in chloroform. This solution was quantitatively analyzed by HPLC to calculate the yield. The yield was 12.1%.

The peak areas (%) of the compounds (1), (2), (4), and (5) in the reaction solution are shown in Table 4. The amount of remained compound (1) as the raw material is large, and the decomposition of product is confirmed with time. It is found that a target is obtained even by a reaction at a pH of 2 to 3. However, the relative ratio of the impurity increases, and the yield of the target tends to decrease.

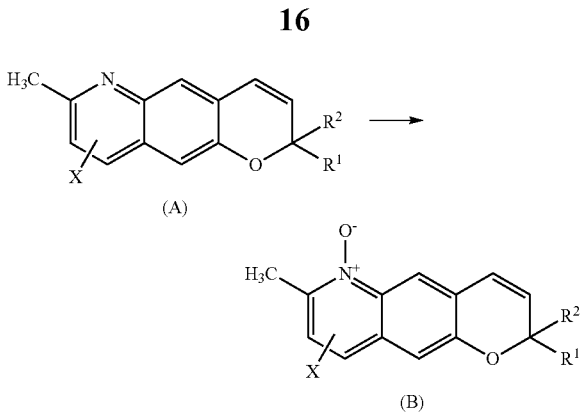

wherein $R^1$ and $R^2$ are each independently a hydrogen atom, a $C_{1-6}$ alkyl group, or a $C_{7-12}$ aralkyl group; and X is a hydrogen atom, a halogen atom, a $C_{1-6}$ alkyl group, a $C_{3-6}$ cycloalkyl group, a $C_{6-10}$ aryl group, a $C_{7-12}$ aralkyl group, a $C_{1-6}$ alkoxy group, a $C_{1-6}$ acyloxy group, or a cyano group, and adjusting the pH of a reaction solution to 4 to 8.

2. The method according to claim 1, wherein the quinoline compound of Formula (A) is 2,2,7,9-tetramethyl-2H-pyrano[2,3-g]quinoline of Formula (1) and the quinoline N-oxide compound of Formula (B) is 2,2,7,9-tetramethyl-2H-pyrano[2,3-g]quinoline N-oxide of Formula (2)

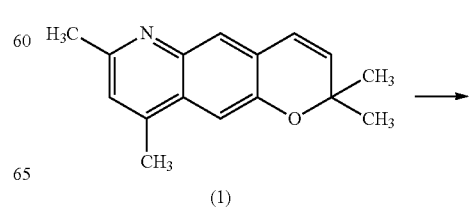

TABLE 4

| | (1) | (2) | (4) | (5) |
|---|---|---|---|---|
| 1 hour of reaction | 1.717 | 37.680 | 1.851 | 51.545 |
| 2 hours of reaction | 1.409 | 35.635 | 2.474 | 50.952 |
| 3 hours of reaction | 1.089 | 33.489 | 2.946 | 50.677 |
| 4 hours of reaction | 0.885 | 31.971 | 3.259 | 50.031 |
| 5 hours of reaction | 0.726 | 30.212 | 3.561 | 49.564 |
| 27 hours of reaction | 0.115 | 16.431 | 1.413 | 43.492 |

INDUSTRIAL APPLICABILITY

According to the present invention, a nitrogen-containing heterocyclic N-oxide compound useful as a raw material for a pharmaceutical product can be safely produced in high yield.

The invention claimed is:

1. A method for producing a quinoline N-oxide compound of Formula (B) comprising reacting a quinoline compound of Formula (A) with a persulfate:

-continued

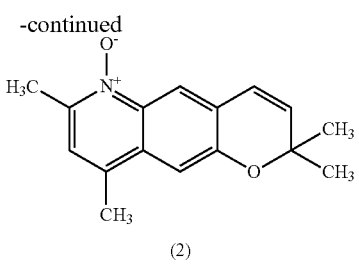

(2)

3. The method according to claim 1, comprising adding a base.

4. The method according to claim 3, wherein the base added is a hydroxide of alkali metal.

5. The method according to claim 4, wherein the base added is potassium hydroxide.

6. The method according to claim 3, wherein the base added is an aqueous solution form of the base.

7. The method according to claim 1, comprising adjusting the pH of a reaction solution to 6 to 7.

8. The method according to claim 1, wherein the persulfate is potassium hydrogen persulfate.

9. The method according to claim 1, wherein the persulfate is a double salt containing potassium hydrogen persulfate.

10. The method according to claim 9, wherein the double salt containing potassium hydrogen persulfate is a double salt of potassium hydrogen persulfate, potassium hydrogen sulfate, and potassium sulfate.

11. The method according to claim 1, wherein the persulfate added has an aqueous solution form.

12. The method according to claim 3, wherein said adjusting comprises (1) adding the persulfate and the base to a reactor containing the quinoline compound of Formula (A), (2) adding the quinoline compound of Formula (A) and the base to a reactor containing the persulfate, or (3) adding the quinoline compound of Formula (A) and the persulfate to a reactor containing the base.

13. The method according to claim 12, wherein said adjusting comprises (1) or (3).

14. The method according to claim 12, wherein said adjusting comprises (1).

* * * * *